US012784185B2

(12) United States Patent
Kim et al.

(10) Patent No.: US 12,784,185 B2
(45) Date of Patent: Nov. 3, 2026

(54) APPARATUS AND METHOD FOR ANALYZING COMPOSITION OF INTERMETALLIC COMPOUNDS

(71) Applicants: SK On Co., Ltd., Seoul (KR); SK Innovation Co., Ltd., Seoul (KR)

(72) Inventors: Hyeong Won Kim, Daejeon (KR); Won Seok Choi, Daejeon (KR)

(73) Assignees: SK On Co., Ltd., Seoul (KR); SK Innovation Co., Ltd., Seoul (KR)

( * ) Notice: Subject to any disclaimer, the term of this patent is extended or adjusted under 35 U.S.C. 154(b) by 160 days.

(21) Appl. No.: 18/983,628

(22) Filed: Dec. 17, 2024

(65) Prior Publication Data

US 2025/0329011 A1 Oct. 23, 2025

(30) Foreign Application Priority Data

Apr. 23, 2024 (KR) ........................ 10-2024-0054085

(51) Int. Cl.
*G06T 7/00* (2017.01)
*G01N 23/04* (2018.01)
(Continued)

(52) U.S. Cl.
CPC ............. *G06T 7/001* (2013.01); *G01N 23/04* (2013.01); *G01N 23/06* (2013.01);
(Continued)

(58) Field of Classification Search
CPC .... G06V 10/56; G06V 2201/06; G06V 20/69; G06V 10/60; G06V 10/24; G06V 10/7715; G06T 7/90; G06T 2207/10061; G06T 7/73; G06T 7/001; G06T 2207/30136; G06T 2207/10024; G06T 11/10; G01N 23/04; G01N 23/2251; G01N 2021/558; G01N 21/8851; G01N 21/25; G01N 33/54346; G01N 21/65; G01N 2223/401;
(Continued)

(56) References Cited

U.S. PATENT DOCUMENTS

| | | | | |
|---|---|---|---|---|
| 11,383,324 B2 * | 7/2022 | Lee | ........................ | B23K 31/12 |
| 11,555,235 B2 * | 1/2023 | Tokuda | ................... | C22C 18/04 |
| 2020/0108462 A1 | 4/2020 | Lee et al. | | |

FOREIGN PATENT DOCUMENTS

| | | |
|---|---|---|
| KR | 10-2017-0058702 A | 5/2017 |
| KR | 10-2019-0029030 A | 3/2019 |

* cited by examiner

*Primary Examiner* — Courtney Joan Nelson
(74) *Attorney, Agent, or Firm* — Jones Day

(57) ABSTRACT

A apparatus for analyzing a composition of an intermetallic compound includes a database storing data of a plurality of feature areas matched to respective composition ratios, a plurality of brightness range data corresponding to the plurality of respective feature areas, and color data, for an intermetallic compound generated during welding of dissimilar metals, a microscope image acquisition unit acquiring an electron microscope image including a brightness value for the intermetallic compound to be analyzed, a signal processor extracting a unit brightness value corresponding to each preset image basic unit from the electron microscope image and searching for color data of a corresponding feature area from the database based on the unit brightness value, and an image processor applying searched color data to the electron microscope image and generating a colorization image.

15 Claims, 19 Drawing Sheets

(51) Int. Cl.
*G01N 23/06* (2018.01)
*G01N 23/2251* (2018.01)
*G01N 33/2028* (2019.01)
*G06T 7/90* (2017.01)
*G06V 10/56* (2022.01)

(52) U.S. Cl.
CPC ..... *G01N 23/2251* (2013.01); *G01N 33/2028* (2019.01); *G06T 7/90* (2017.01); *G06V 10/56* (2022.01); *G01N 2223/401* (2013.01); *G06T 2207/10024* (2013.01); *G06T 2207/10061* (2013.01); *G06T 2207/30136* (2013.01); *G06V 2201/06* (2022.01)

(58) Field of Classification Search
CPC ......... G01N 2223/418; G01N 33/2028; G01N 33/553; G01N 2223/629; G01N 33/20; G01N 2021/8472; G01N 33/0036; G01N 23/06
See application file for complete search history.

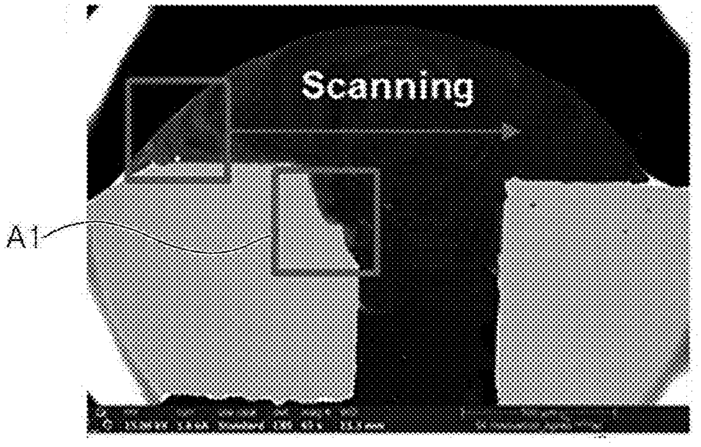
FIG. 4A
A1
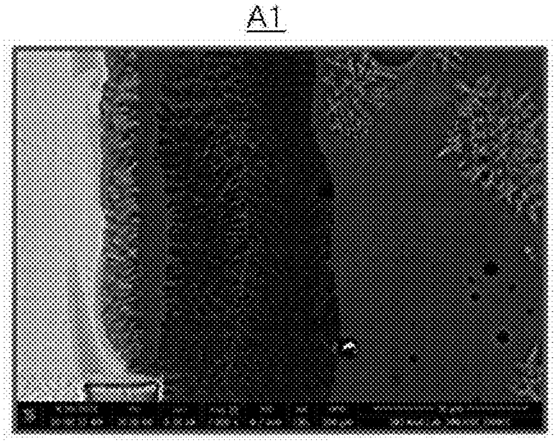
SHAPE ANALYSIS IMAGE
USING SEM BSE IMAGE
FIG. 4B
A1
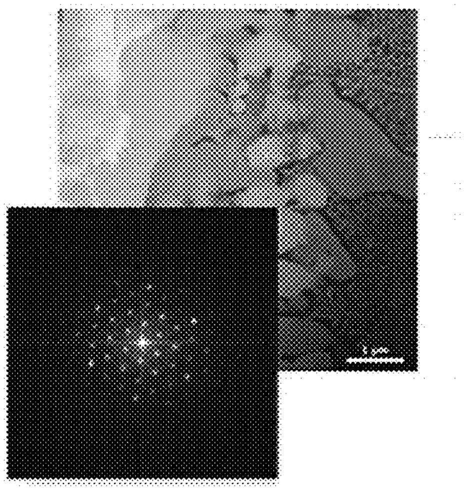
PHASE ANALYSIS IMAGE
PER FEATURE AREA BY TEM ANALYSIS
FIG. 4C
| | Al | Cu |
|---|---|---|
| at. % | X% | Y% |
FIG. 4D

APPARATUS AND METHOD FOR ANALYZING COMPOSITION OF INTERMETALLIC COMPOUNDS

CROSS-REFERENCE TO RELATED APPLICATION(S)

This patent document claims the priority and benefits of Korean Patent Application No. 10-2024-0054085 filed on Apr. 23, 2024, the disclosure of which is incorporated herein by reference in its entirety.

TECHNICAL FIELD

The disclosure and implementations disclosed in this patent document generally relate to a apparatus and method for analyzing a composition of an intermetallic compound.

BACKGROUND

In general, welding is performed to electrically connect the tab (for example, aluminum) and busbar (for example, copper) of a battery cell.

In dissimilar metal welding between dissimilar metals (for example, a copper tab and an aluminum busbar), high temperatures may cause two or more materials to join together, forming intermetallic compounds (IMCs).

Intermetallic compounds (IMCs) may be generated in a wide variety of ways depending on a combination ratio of the materials and generation temperature.

Accordingly, such intermetallic compound generation is known to be a major factor in causing cracks in the weld and reducing the weld quality, and analyzing the composition of intermetallic compounds (IMCs) is an important factor in the quality analysis of dissimilar welding.

This related art analysis method for intermetallic compounds (IMCs) uses a scanning electron microscope (SEM) and a transmission electron microscope (TEM), and in such existing methods, the analysis of intermetallic compounds (IMCs) may be conducted through quantitative tissue analysis of a very small area of the weld.

The related art analysis method for intermetallic compounds (IMCs) is a direct analysis method that requires a large amount of time to obtain microscope images and related information for each weld and to use these microscope images and related information.

Accordingly, the related art analysis method has the problem that it requires a large amount of time to analyze all areas of the weld, and thus it is difficult to quickly perform quantitative analysis of the entire area of the weld, and it is difficult to perform intuitive quantitative analysis of weld quality of the weld.

SUMMARY

The present disclosure may be implemented in some embodiments to provide a apparatus and method for analyzing a composition of an intermetallic compound, in which quantitative analysis, such as colorization or the like for each feature area, on an intermetallic compound (OBT) as an analysis target, may be performed by utilizing a database (DB) storing related information necessary for analysis of intermetallic compounds (IMCs) in advance.

In some embodiments, a apparatus for analyzing a composition of an intermetallic compound includes a database storing data of a plurality of feature areas matched to respective composition ratios, a plurality of brightness range data corresponding to the plurality of respective feature areas, and color data, for an intermetallic compound generated during welding of dissimilar metals; a microscope image acquisition unit acquiring an electron microscope image including a brightness value for the intermetallic compound to be analyzed; a signal processor extracting a unit brightness value corresponding to each preset image basic unit from the electron microscope image and searching for color data of a corresponding feature area from the database based on the unit brightness value; and an image processor applying searched color data to the electron microscope image and generating a colorization image.

In some embodiments, a method of analyzing a composition of an intermetallic compound includes a DB construction operation of constructing, by a apparatus for analyzing a composition of an intermetallic compound, a database storing data of a plurality of feature areas matched to respective composition ratios, and color data and a plurality of brightness range data corresponding to the plurality of respective feature areas, for the intermetallic compound generated during welding of dissimilar metals; a microscope image acquisition operation of acquiring an electron microscope image including a brightness value for the intermetallic compound as an analysis target, by the apparatus for analyzing a composition of an intermetallic compound; a signal processing operation of extracting a unit brightness value corresponding to each of preset image basic units from the electron microscope image and searching for color data of a corresponding feature area from the database based on the unit brightness value, by the apparatus for analyzing a composition of an intermetallic compound; and an image processing operation of applying searched color data to the electron microscope image and generating a colorization image by the apparatus for analyzing a composition of an intermetallic compound.

In addition, it can be understood that aspects of the present disclosure are not limited to the aspects illustrated above and that other aspects may be additionally provided in the description below.

BRIEF DESCRIPTION OF DRAWINGS

Certain aspects, features, and advantages of the present disclosure are illustrated by the following detailed description with reference to the accompanying drawings.

FIG. 4A is an illustrative diagram of an original image for intermetallic compounds (IMCs), FIG. 4B is an illustrative diagram of a shape analysis image of an intermetallic compound using a BSE image by SEM, FIG. 4C is an illustrative diagram of a phase analysis image by feature area of an intermetallic compound using an image by TEM, and FIG. 4D is an illustrative diagram of an EDS composition analysis.

In the drawings and detailed descriptions, the same reference numerals refer to the same components. The drawings may not be to scale, and the relative sizes, proportions, and depictions of drawing elements may be exaggerated for clarity, explanation, and convenience.

DETAILED DESCRIPTION

Figure 1:
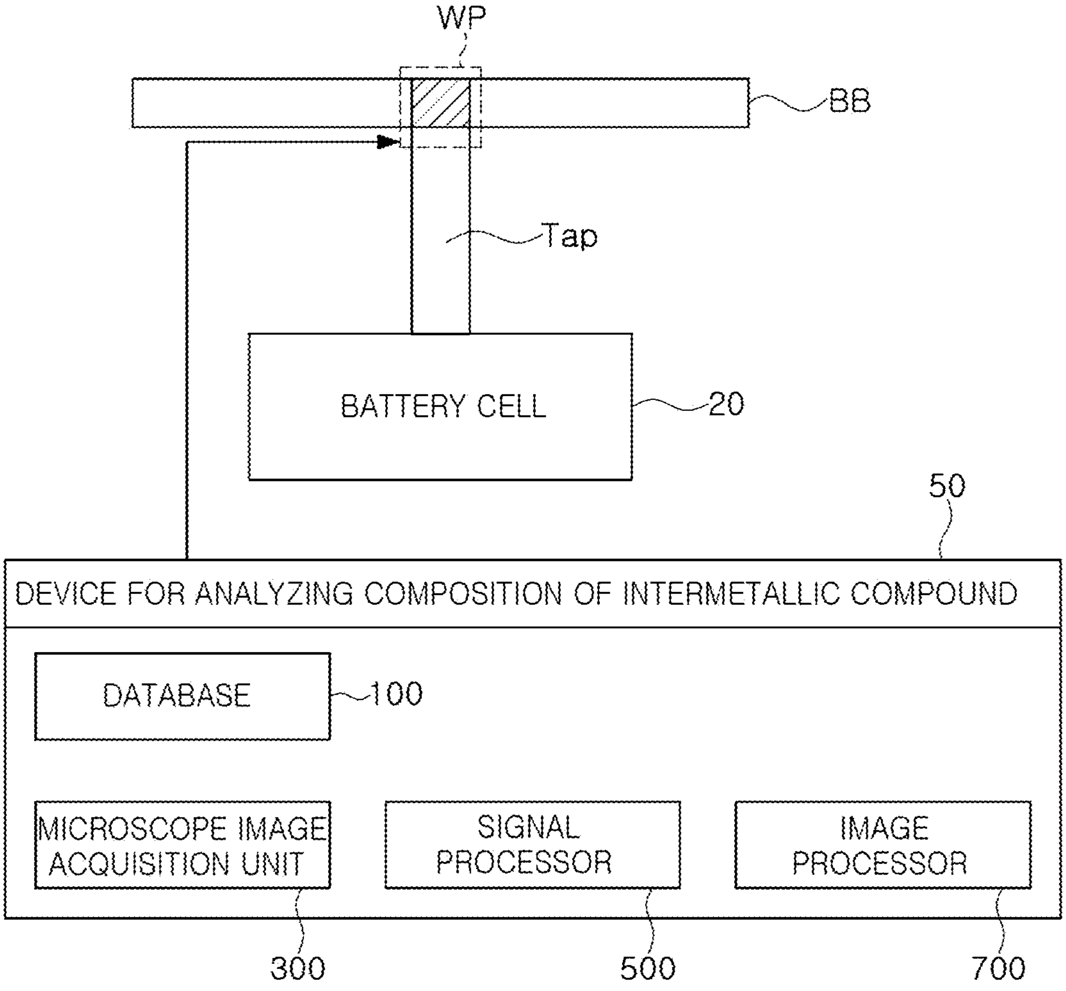
FIG. 1 is a schematic diagram of a apparatus for analyzing a composition of an intermetallic compound according to an embodiment.

Features of the present disclosure disclosed in this patent document are described by example embodiments with reference to the accompanying drawings.

Hereinafter, embodiments will be further described with reference to detailed experimental examples. The embodiments and comparative examples included in the experimental examples are merely illustrative of the present disclosure and do not limit the scope of the appended claims. It is obvious to those skilled in the art that various changes and modifications to the embodiments are possible within the scope and technical idea of the present disclosure, and it is also natural that such changes and modifications fall within the scope of the appended claims.

The present disclosure may have various modifications and various embodiments, and specific embodiments are illustrated in the drawings and described in detail. However, this is not intended to limit the present disclosure to specific embodiments, and it should be understood that all modifications, equivalents, or substitutes included in the scope and idea of the present disclosure are included.

The terms first, second, etc. may be used to describe various components, but the components should not be limited by the terms. The terms are used only for the purpose of distinguishing one component from another. For example, without departing from the scope of the present disclosure, a first component may be referred to as a second component, and similarly, a second component may also be referred to as a first component. The term "and/or" includes a combination of a plurality of related described items or any of a plurality of related described items.

The terms used in this application are used only to describe specific embodiments and are not intended to limit the present disclosure. The singular expression includes the plural expression unless the context clearly indicates otherwise. In this application, the terms "includes", "has" and the like are intended to specify the presence of a feature, number, step, operation, component, part, or combination thereof described in the specification, but should be understood not to preclude the possibility of the presence or addition of one or more other features, numbers, steps, operations, components, parts, or combinations thereof.

Unless otherwise defined, all terms used herein, including technical or scientific terms, have the same meaning as commonly understood by one of ordinary skill in the art to which this disclosure belongs. Terms defined in commonly used dictionaries should be interpreted as having a meaning consistent with the meaning they have in the context of the relevant technology, and shall not be interpreted in an ideal or overly formal sense unless explicitly defined in this application.

Hereinafter, with reference to the attached drawings, embodiments will be described in more detail.

FIG. 1 is a schematic diagram of a apparatus for analyzing a composition of an intermetallic compound according to an embodiment.

Referring to FIG. 1, a apparatus 50 for analyzing a composition of an intermetallic compound according to an embodiment may include a database 100, a microscope image acquisition unit 300, a signal processor 500, and an image processor 700 to perform an analysis on a composition of an intermetallic compound (OBT) generated at a weld (WP) between a tab (Tab) of a battery cell 20 and a busbar (BB). This will be described with reference to FIGS. 2 to 16.

Meanwhile, the battery cell of the present disclosure may be built into a battery module or may be built into a battery pack. In the present disclosure, the battery cell applied is not limited to a particular structure or type as long as it is welded to a busbar by including a tab.

In addition, the present disclosure is described with respect to a T-joint-shaped weld between a tab (Tab) of a battery cell 20 and a busbar (BB) as an example, but is not limited thereto.

Figure 2:
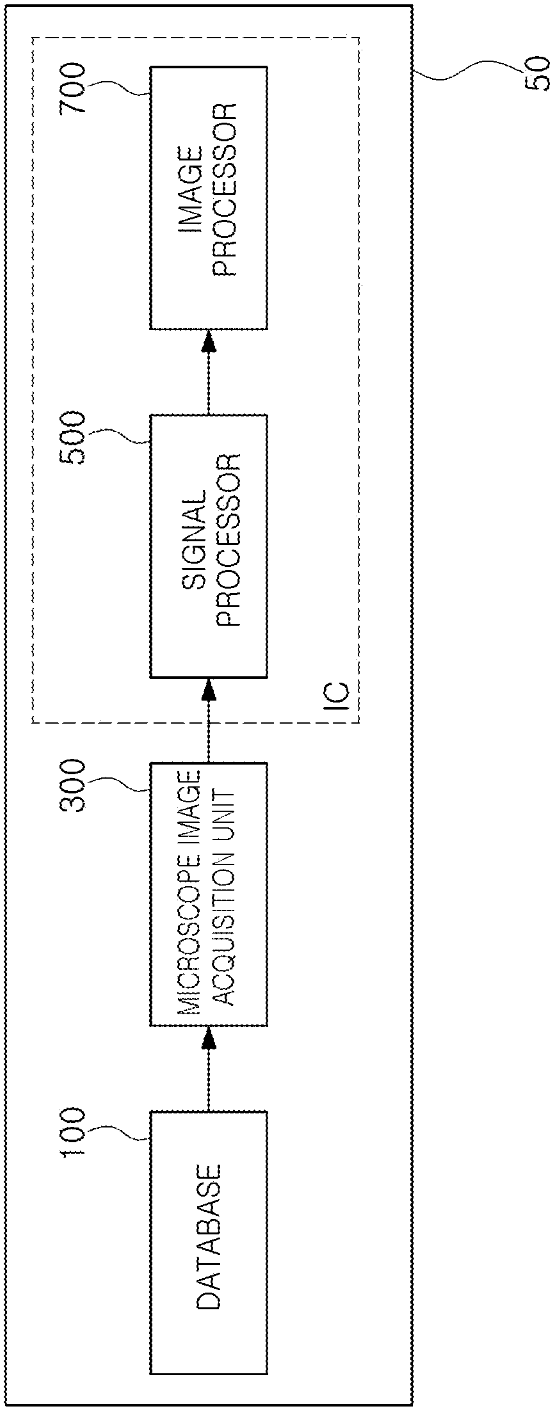
FIG. 2 is an illustrative diagram of a apparatus for analyzing a composition of an intermetallic compound according to an embodiment.

FIG. 2 is an illustrative diagram of a apparatus for analyzing a composition of an intermetallic compound according to an embodiment.

Referring to FIGS. 1 and 2, a apparatus for analyzing a composition of an intermetallic compound according to an embodiment includes, as described above, a database 100, a microscope image acquisition unit 300, a signal processor 500, and an image processor 700.

Referring to FIG. 2, the database 100 may store, for intermetallic compounds (IMCs) generated during welding of dissimilar metals, data (PI) of a plurality of feature areas (for example, FA1 to FA5) matched to respective composition ratios (CR in FIG. 3), and a plurality of brightness range data (BI) corresponding to the plurality of respective feature areas (for example, FA1 to FA5), and color data (HI). For example, in the database 100, a plurality of feature areas FA1 to FA5, a composition ratio (CR), and color data (HI) may be respectively matched based on a plurality of brightness range data (BI). For example, when the intermetallic compound (IMCs) is composed of aluminum (Al) and copper (Cu), the composition ratio (CR) may be the ratio of aluminum (Al) and copper (Cu). The database 100 will be described in more detail with reference to FIGS. 3, 4A to 4D, and 10.

The microscope image acquisition unit 300 may acquire an electron microscope image (IEM) including a brightness value for the intermetallic compound (OBT) that is the analysis target.

For example, the microscope image acquisition unit 300 may receive an electron microscope image (IEM) including a brightness value for the intermetallic compound (OBT) from the outside, and may include a function that may generate the electron microscope image (IEM) on its own, and the present disclosure is not limited to a specific example. For example, the electron microscope image (IEM) may be a microscope image including different brightness values depending on the composition ratio of the intermetallic compound (OBT). The microscope image acquisition unit 300 will be described in more detail with reference to FIGS. 5 and 6.

The signal processor 500 may extract a unit brightness value BV1 corresponding to each preset image basic unit (RU) from the electron microscope image (IEM), and search for color data (HI) of the corresponding feature area from the database 100 based on the unit brightness value BV1. For example, the preset image basic unit (RU) may be at least one pixel. For example, the image basic unit (RU) may be one pixel, or the image basic unit (RU) may include two or more pixels.

Hereinafter, in the present disclosure, a case in which the image basic unit (RU) is a pixel may be described, but is not limited thereto. The signal processor 500 will be described in more detail with reference to FIGS. 7, 8A and 8B, and 9.

The image processor 700 may apply searched color data (HI) to the electron microscope image (IEM) to generate a colorization image (ICR). For example, the image processor 700 may generate a colorization image (ICR) by reflecting the corresponding color data (HI) in each of a plurality of feature areas (for example, FA1 to FA5) analyzed for the electron microscope image (IEM). The image processor 700 will be described in more detail with reference to FIGS. 10 to 15.

In the present disclosure, each of the signal processor 500 and the image processor 700 may be implemented as hardware or software in at least one integrated circuit (IC) built into the apparatus 50 for analyzing a composition of an intermetallic compound, and is not particularly limited to either one.

In addition, the signal processor 500 and the image processor 700 may be implemented as individual processors, or may be implemented as one processor, and is not particularly limited to either one.

For respective drawings of the present disclosure, unnecessary redundant descriptions of components with the same symbols and functions may be omitted, and possible differences between respective drawings may be described.

Figure 3:
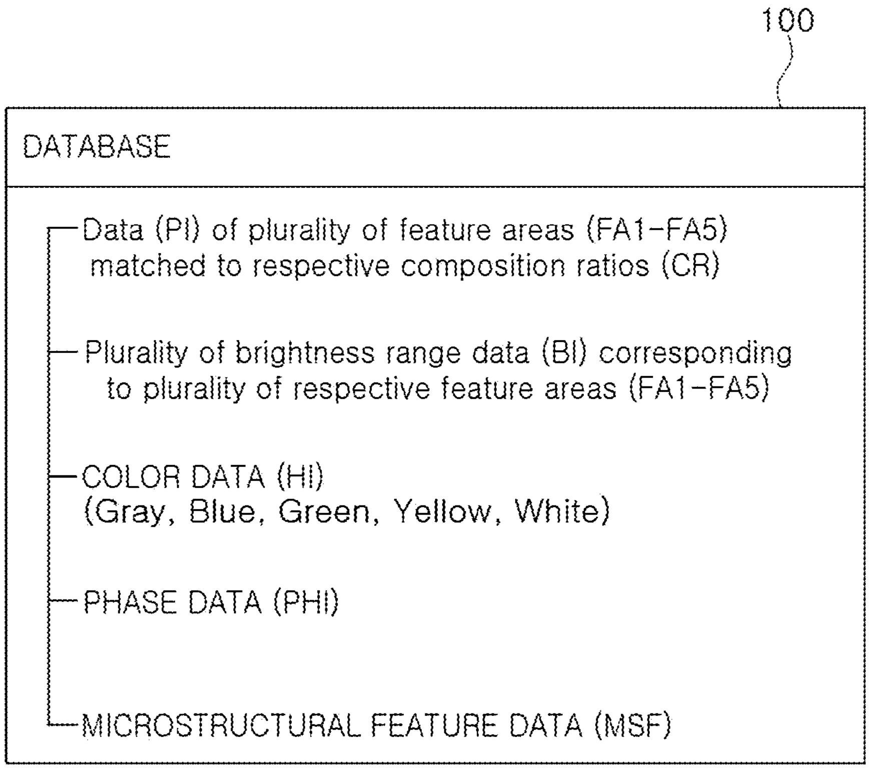
FIG. 3 is an illustrative diagram of a database.

FIG. 3 is an example of a database.

Referring to FIG. 3, the database 100 may include data (PI) of a plurality of feature areas (for example, FA1 to FA5) matched to respective composition ratios (CR) described above, a plurality of brightness range (BR) data (BI) and color data (HI), for the intermetallic compounds (IMCs) generated during welding of dissimilar metals, and in addition, may further include phase data (PHI) and microstructural feature data (MSF) according to each composition ratio (CR).

For example, in the database 100, a plurality of feature areas (for example, FA1 to FA5) may be defined by an adjustment ratio. For example, when the plurality of feature areas (for example, FA1 to FA5) include first to fifth feature areas FA1 to FA5, the first feature area FA1 may be defined as a 100% aluminum region (Al), the second, third and fourth feature areas FA2, FA3 and FA4 may be defined as regions where aluminum (Al) and copper (Cu) are mixed, and the fifth feature area FA5 may be defined as a 100% copper region.

For example, the first feature area FA1 may have a copper (Cu) ratio of more than 0% and less than or equal to Y1%, the second feature area FA2 may have a copper (Cu) ratio of more than Y1% and less than or equal to Y2%, the third feature area FA3 may have a copper (Cu) ratio of more than Y2% and less than or equal to Y3%, the fourth feature area FA4 may have a copper (Cu) ratio of more than Y3% and less than or equal to Y4%, and the fifth feature area FA5 may have a copper (Cu) ratio of more than Y4% and less than or equal to 100%, and the examples of the composition ratios above are only an example and are not limited thereto.

In the present disclosure, a plurality of feature areas (for example, FA1 to FA5) may be preset in consideration of aspects in which characteristics related to weld soundness, such as thermochemical stability, crack susceptibility or crack resistance, are distinguished from each other according to the composition ratio of metal elements (for example, aluminum (Al) and copper (Cu)) constituting intermetallic compounds (IMCs).

In the present disclosure, a phase may be defined as a region of a chemically identical, physically distinct, and mechanically separable material. For example, even if the chemical composition is the same, the gas phase and the liquid phase may be different phases, such as water and ice. The phase of an intermetallic compound (IMCs) may be the same phase when the chemical composition and lattice structure thereof are the same.

In addition, the average composition of the plurality of feature areas FA1 to FA5 may be determined by the chemical composition and phase fraction of the respective constituent intermetallic compounds (IMCs).

For example, the color data (HI) may include gray, blue, green, yellow, and white, which are respectively matched to the first to fifth feature areas FA1 to FA5.

For example, when the plurality of feature areas FA1 to FA5 include a first feature area FA1, a second feature area FA2 and a third feature area FA3, the first feature area FA1 may be formed such that the first intermetallic compound IMC1 and the second intermetallic compound IMC2 have a microstructural feature A, and an average composition range of the area may be $a<x\leq b$. The second feature area FA2 may be formed such that the first intermetallic compound IMC1 and the third intermetallic compound IMC3 have a microstructural feature B, and an average composition range of the area may be $b<x\leq c$. The third feature area FA3 may be formed such that the first intermetallic compound IMC1, the second intermetallic compound IMC2, and the third intermetallic compound IMC3 have a microstructural feature C, and an average composition range of the area may be $c<x\leq d$. In this case, a, b, c and d are ratios set in advance, and x may be copper (Cu) or aluminum (Al). An example thereof is explained with reference to Table 1 below.

For example, the database 100 may match a correction brightness value BV2 of the brightness range data (BI) and the color of the color data (HI) with each other based on a plurality of feature areas FA1 to FA5 of the preset feature area data (PI) and store the same as illustrated in Table 1 below.

TABLE 1

| Feature area (composition ratio) (Cu at %) | Brightness range data (BI) <Correction brightness value><BV2> | Color data (HI) |
|---|---|---|
| FA1 (0% ≤ Cu at % ≤ Y1 % ) | A ≤ BV2 < B*Y1/100 + A*(1-Y1/100) | Gray |
| FA2 (Y1 % < Cu at % ≤ Y2 % ) | B*Y1/100 + A*(1-Y1/100) ≤ BV2 < B*Y2/100 + A*(1-Y2/100) | Blue |
| FA3 (Y2 % < Cu at % ≤ Y3 % ) | B*Y2/100 + A*(1-Y2/100) ≤ BV2 < B*Y3/100 + A*(1-Y3/100) | Green |
| FA4 (Y3 % < Cu at % ≤ Y4 % ) | B*Y3/100 + A*(1-Y3/100) ≤ BV2 < B*Y4/100 + A*(1-Y4/100) | Yellow |
| FA5 (Y4 % < Cu at % ≤ 100% ) | B*Y4/100 + A*(1-Y4/100) ≤ BV2 < B | White |

Referring to Table 1 above, the correction brightness value BY2 will be described. For example, in the case of dissimilar welding including aluminum (Al) and copper (Cu), if the average brightness of aluminum (Al) is 'A' and the average brightness of copper (Cu) is 'B', the brightness range in the dissimilar welding may be between 'A' and 'B', and in this case, the brightness range data may be expressed as in Table 1 above depending on the composition (%) of copper (Cu). For example, referring to Table 1 above, the correction brightness value for a case in which the copper (Cu) content is Y2% may be 'B*Y2/100+A*1-Y2/100'.

FIG. 4A is an example of an original image of an intermetallic compound (IMC), FIG. 4B is an example of a shape analysis image of an intermetallic compound using a BSE image by SEM, FIG. 4C is an example of a phase analysis image by feature areas of an intermetallic compound using an image by TEM, and FIG. 4D is an example of a composition analysis image by Energy Dispersive Spectroscopy (EDS) analysis.

The image analyzed through SEM for the A1 area of the original image of the intermetallic compound (IMC) illustrated in FIG. 4A is illustrated in FIG. 4B, and the image analyzed through TEM for the A1 area of the original image of FIG. 4A is illustrated in FIG. 4C.

The image illustrated in FIG. 4B is an image of a shape analysis of an intermetallic compound using a BSE image by SEM for the A1 area of the original image of FIG. 4A. The shape analysis image illustrated in FIG. 4B is comprised of many feature areas where shapes are distinguishable from each other, and these many feature areas may be set more simply as a plurality of feature areas FA1 to FA5.

The image illustrated in FIG. 4C is a composition analysis image of an intermetallic compound using an electron microscope image by TEM for the A1 area of the original image of FIG. 4A. The composition analysis image illustrated in FIG. 4C is comprised of many feature areas where microstructural features are distinguished from each other, and these many feature areas may be set to be distinguished as phase analysis data for respective feature areas FA1 to FA5.

The table illustrated in FIG. 4D is a table illustrating composition analysis by Energy Dispersive Spectroscopy (EDS) analysis. The composition analysis table illustrated in FIG. 4D includes a composition ratio (%) expressed as an element ratio (at. %) for aluminum (Al) and copper (Cu). For example, X and Y in FIG. 4D may be aluminum (Al) and copper (Cu).

Figure 5A:
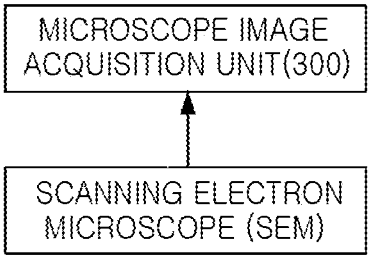
FIG. 5A and FIG. 5B are an illustrative diagram of an image acquisition unit of a microscope image acquisition unit.
Figure 5B:
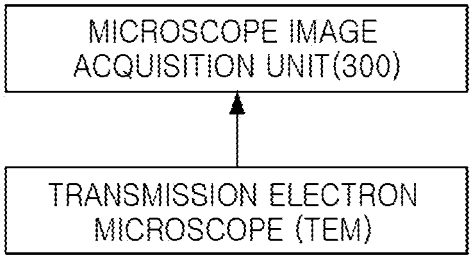

FIGS. 5A and 5B are examples of an image acquisition diagram of a microscope image acquisition unit.

Referring to FIGS. 5A and 5A, the microscope image acquisition unit 300 may acquire an electron microscope image (IEM) of the intermetallic compound (OBT) through a Scanning Electron Microscope (SEM) or a Transmission Electron Microscope (TEM), and the present disclosure is not limited thereto, and any electron microscope capable of generating an electron microscope image (IEM) including a brightness value for the intermetallic compound (OBT) may be used.

For example, when the electron microscope image (IEM) is acquired by a SEM, shape data for a plurality of respective feature areas FA1 to FA5 with respect to the intermetallic compound (OBT) may be included.

In addition, when the electron microscope image (IEM) is acquired by a TEM, phase analysis data for a plurality of respective feature areas FA1 to FA5 with respect to the intermetallic compound (OBT) may be included.

Figure 6:
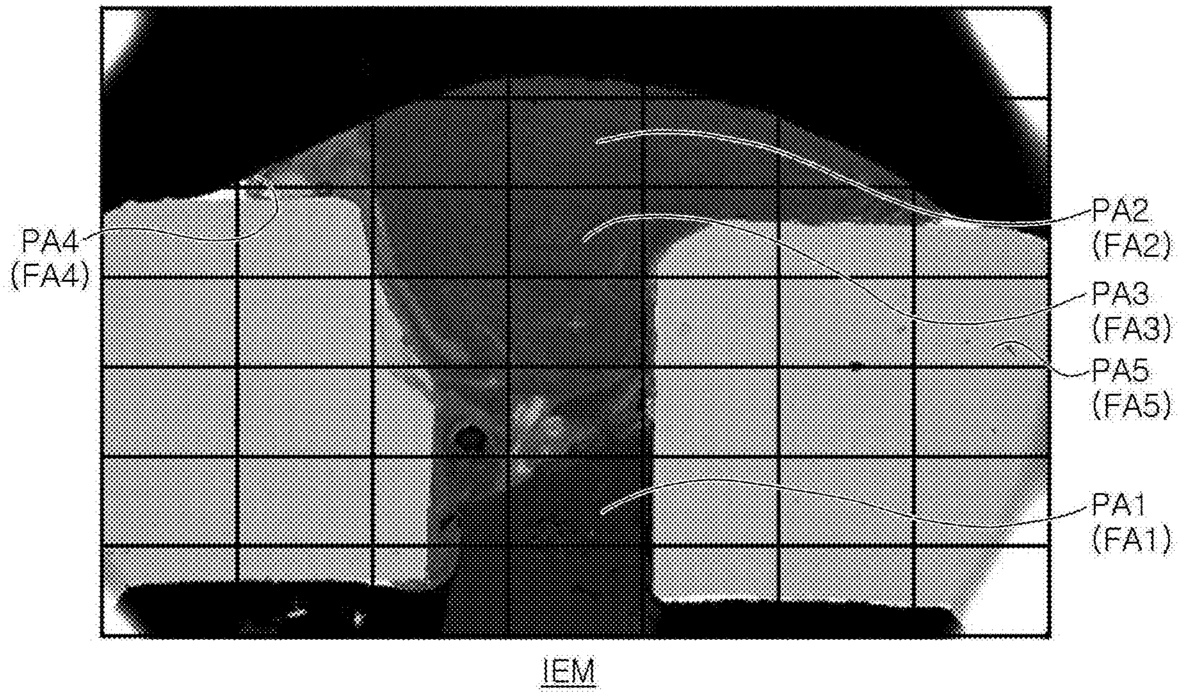
FIG. 6 is an illustrative diagram of an electron microscope image (IEM).

FIG. 6 is an example of an electron microscope image (IEM).

Referring to FIG. 6, an electron microscope image (IEM) in the present disclosure may include different brightness values depending on a composition ratio of metal elements included in an intermetallic compound (OBT) that is an analysis target. For example, an electron microscope image (IEM) is comprised of pixel units, and if the composition ratios of the intermetallic compound (OBT) corresponding to respective pixels are different, the brightness values for respective pixels may be different.

For example, when the intermetallic compound (OBT) is comprised of aluminum (Al) and copper (Cu), an electron microscope image (IEM) for the intermetallic compound (OBT) may have a brightness value determined depending on the composition ratio of aluminum (Al) and copper (Cu).

For example, the brightness value for each pixel may be any value within the range of 0 (zero) to 255, and if, for example, the brightness value range is normalized to 1 to 100, the brightness value of each pixel may be any value within the range of 0 (zero) to 100, which is the normalized brightness value range. In the PA1 area (corresponding to FA1 in FIG. 3) of the electron microscope image (IEM), when the copper (Cu) ratio is 0% (for example, 0% or more and Y1% or less) and the aluminum ratio is 100% (for example, 100% or less and 97% or more), the brightness value may be 0, in the PA2 area (corresponding to FA2 in FIG. 3) of the electron microscope image (IEM), when the copper (Cu) ratio is greater than 0% (for example, greater than Y1%) and Y2% or less, the brightness value may be greater than 0 and 22 or less, in the PA3 area (corresponding to FA3 in FIG. 3) of the electron microscope image (IEM), when the copper (Cu) ratio is greater than Y2% and Y3% or less, the brightness value may be greater than 22 and 60 or less, and in the PA4 area (corresponding to FA4 in FIG. 3) of the electron microscope image (IEM), when the copper (Cu) ratio is greater than Y3% and Y4% or less, the brightness value may be greater than 60 and 80 or less. In addition, the PA5 area (corresponding to FA5 in FIG. 3) of the electron microscope image (IEM) may have a brightness value of 100 when the copper (Cu) ratio is 100% (for example, 100% or less but more than 80%) and the aluminum ratio is 0% (for example, 0% or more but 20% or less).

Figure 7:
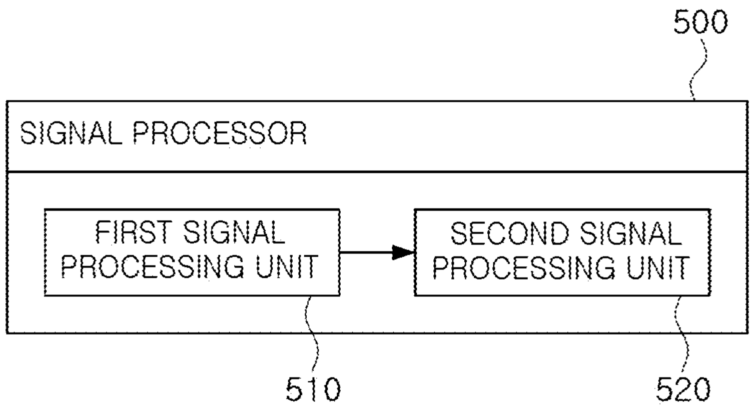
FIG. 7 is an illustrative diagram of a signal processor.

FIG. 7 is an example diagram of a signal processor.

Referring to FIG. 7, the signal processor 500 may include a first signal processing unit 510 and a second signal processing unit 520.

The first signal processing unit 510 may extract a unit brightness value BV1 corresponding to each preset image basic unit (RU) from the electron microscope image (IEM), and may generate a correction brightness value BV2 by correcting the unit brightness value BV1. For example, when the image basic unit (RU) is a pixel, the unit brightness value BV1 may be a brightness value of the corresponding pixel. As another example, when the image basic unit (RU) is a plurality of pixels, the unit brightness value BV1 may be an average brightness value for the plurality of pixels.

The second signal processing unit 520 may check the brightness range data (BI) matched to the correction brightness value BV2 from the database 100 and search for the corresponding color data (HI).

For example, the brightness range data (BI) is as illustrated in Table 1 above, and for the convenience of understanding and explanation, if it is simply expressed in numbers, for example, in the case in which the brightness range data includes a first brightness value range (0≤BV2≤0.2), a second brightness value range (0.2<BV2≤0.4), a third brightness value range (0.4<BV2<0.6), a fourth brightness value range (0.6<BV2≤0.8), and a fifth brightness value range (0.8<BV2≤ 1); for example, when the correction brightness value BV2 is 0.5, this is included in the third brightness value range (0.4<BV2≤0.6), and therefore, corresponds to the third feature area (FA3 (Y2%<Cu at %<Y3%)), and the color may correspond to green.

In this manner, the signal processor 500 may obtain the correction brightness value for each pixel of the electron microscope image (IEM), and may check the feature area and color corresponding to each pixel through the database, using the correction brightness value.

Figure 8A:
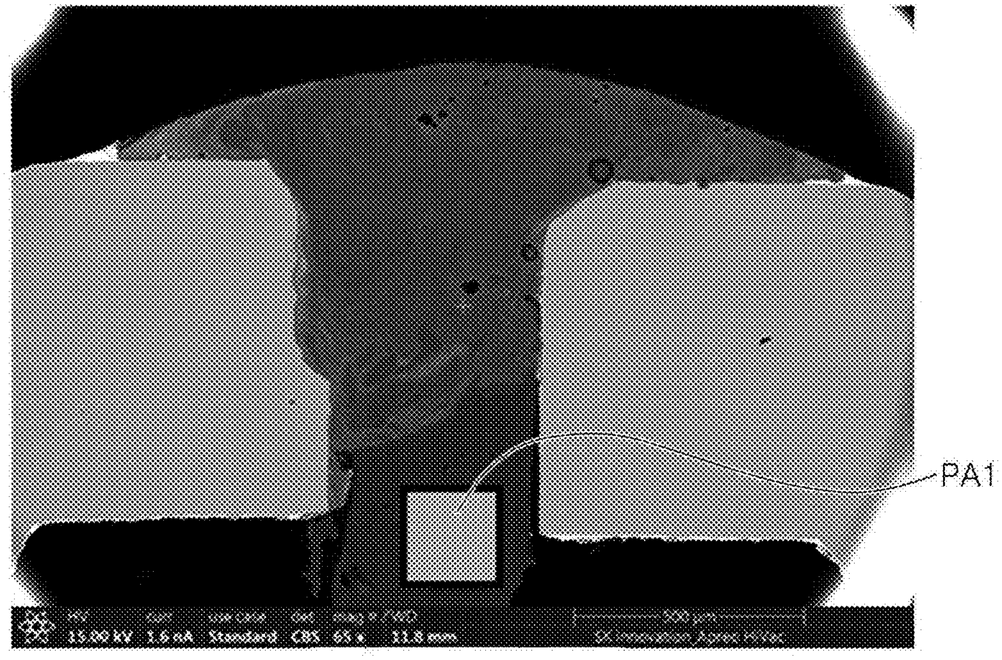
FIG. 8A is an example diagram of an electron microscope image (IEM) having brightness values.
Figure 8B:
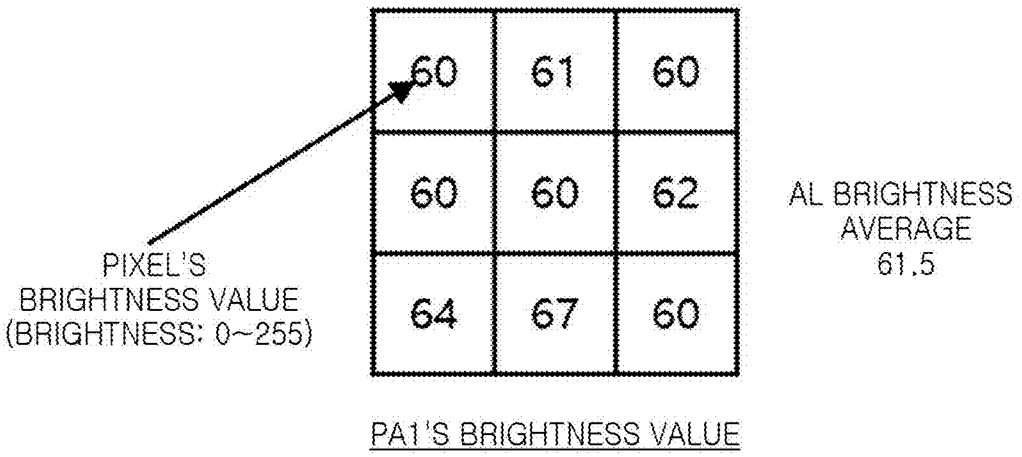
FIG. 8B is an example diagram of a unit brightness value BV1 per pixel for a PA1 area of the electron microscope image (IEM).

FIG. 8A is an example diagram for an electron microscope image (IEM) having a brightness value, and FIG. 8B is an example diagram for a unit brightness value BV1 per pixel for the PA1 area of the electron microscope image (IEM).

The electron microscope image (IEM) illustrated in FIG. 8A may include different brightness values depending on the composition ratio of the intermetallic compound, and the unit brightness value BV1 for the PA1 area corresponding to the bead is as illustrated in FIG. 8B.

Referring to FIG. 8B, when the PA area corresponding to a bead is comprised of 9 pixels, the brightness value of each pixel may be 60 to 67, and the average brightness value of the 9 pixels may be 61.5.

The unit brightness value BV1 in the present disclosure may be a brightness value for one pixel, or may be an average value for a plurality of pixels (for example, 9 pixels), as illustrated in FIG. 8B, and the example for the unit brightness value BV1 is only an example, and the present disclosure is not limited to the example.

Figure 9:
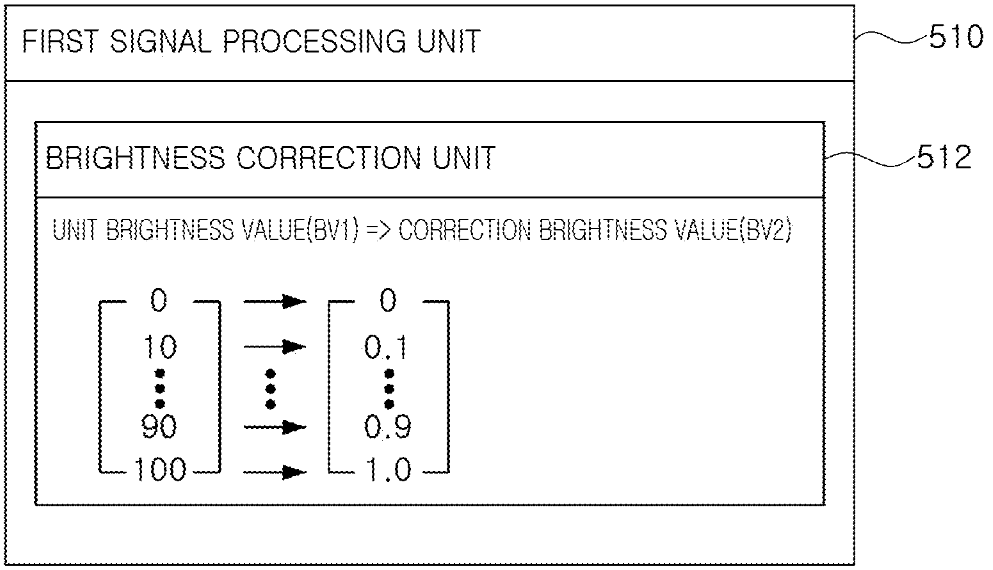
FIG. 9 is an example diagram of a brightness correction unit of a first signal processing unit.

FIG. 9 is an example of a brightness correction unit of the first signal processing unit.

Referring to FIG. 9, the first signal processing unit 510 may include a brightness correction unit 512.

When the intermetallic compound (OBT) is a compound of copper (Cu) and aluminum (Al), the brightness correction unit 512 may correct the unit brightness value BV1 for the intermetallic compound (OBT) to a corresponding correction brightness value BV2 corresponding to a composition ratio of the copper (Cu) and the aluminum (Al), within a range of a preset correction brightness value BV2.

For example, the unit brightness values BV1 of 0, 10, . . . , 90, and 100 may be corrected to the correction brightness values BV2 of 0, 0.1, . . . , 0.9, and 1.0 by the brightness correction unit 512.

Figure 10:
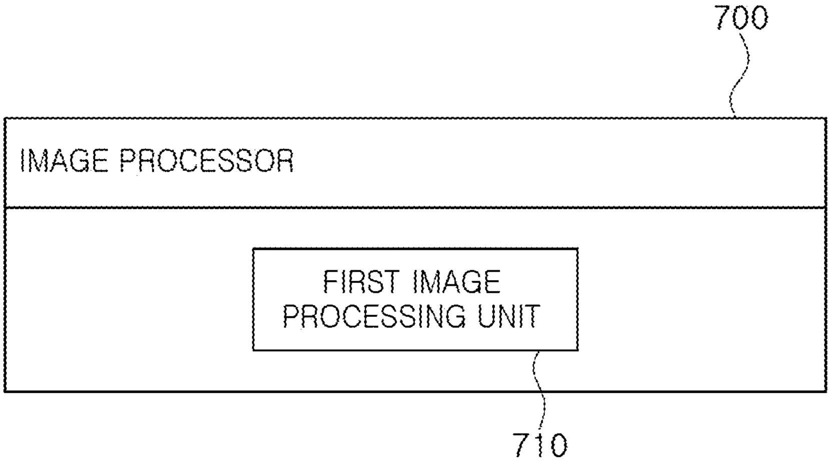
FIG. 10 is an example diagram of an image processor.

FIG. 10 is an example of an image processor.

Referring to FIG. 10, the image processor 700 may include a first image processing unit 710.

The first image processing unit 710 may apply the searched color data (HI) to the electron microscope image (IEM) to generate a colorization image (ICR).

For example, the first image processing unit 710 may identify a color corresponding to each pixel having a brightness value, with respect to all pixels of the electron microscope image (IEM), using a brightness range as a parameter, and may apply the corresponding color to the electron microscope image (IEM) using the corresponding color for each pixel, to generate a colorization image (ICR).

Meanwhile, a table stored in the database 100 by the first image processing unit 710 to generate a colorization image (ICR) may be expressed as, for example, Table 2 below.

Referring to Table 2 below, the database 100 may include a table having feature area data (PI) (FA1 to FA5) and color data (HI) matched to preset brightness range data (BI) (correction brightness value: BV2).

TABLE 2

| Brightness range data (BI) <Correction brightness value><BV2> | Feature area (composition ratio)(Cu at %) | Color data (HI) |
|---|---|---|
| A ≤ BV2 ≤ B*Y1/100 + A*(1-Y1/100) | FA1 (0% ≤ Cu at % ≤ Y1 % ) | Gray |
| B*Y1/100 + A*(1-Y1/100) < BV2 ≤ B*Y2/100 + A*(1-Y2/100) | FA2 (Y1 % < Cu at % ≤ Y2 % ) | Blue |
| B*Y2/100 + A*(1-Y2/100) < BV2 ≤ B*Y3/100 + A*(1-Y3/100) | FA3 (Y2 % < Cu at % ≤ Y3 % ) | Green |
| B*Y3/100 + A*(1-Y3/100) < BV2 ≤ B*Y4/100 + A*(1-Y4/100) | FA4 (Y3 % < Cu at % ≤ Y4 % ) | Yellow |
| B*Y4/100 + A*(1-Y4/100) < BV2 ≤ B | FA5 (Y4 % < Cu at % ≤ 100% ) | White |

As indicated in the above Table 2, referring to the table stored in the database 100, the first image processing unit 710 may confirm the feature area, composition ratio, and color data matched to the brightness range data (BI) through the database 100, and may generate a colorization image (ICR) using the color data corresponding to the corresponding brightness value of each pixel of the electron microscope image (IEM). In the above Table 2, the overlapping content with the above Table 1 is omitted.

Figure 11:
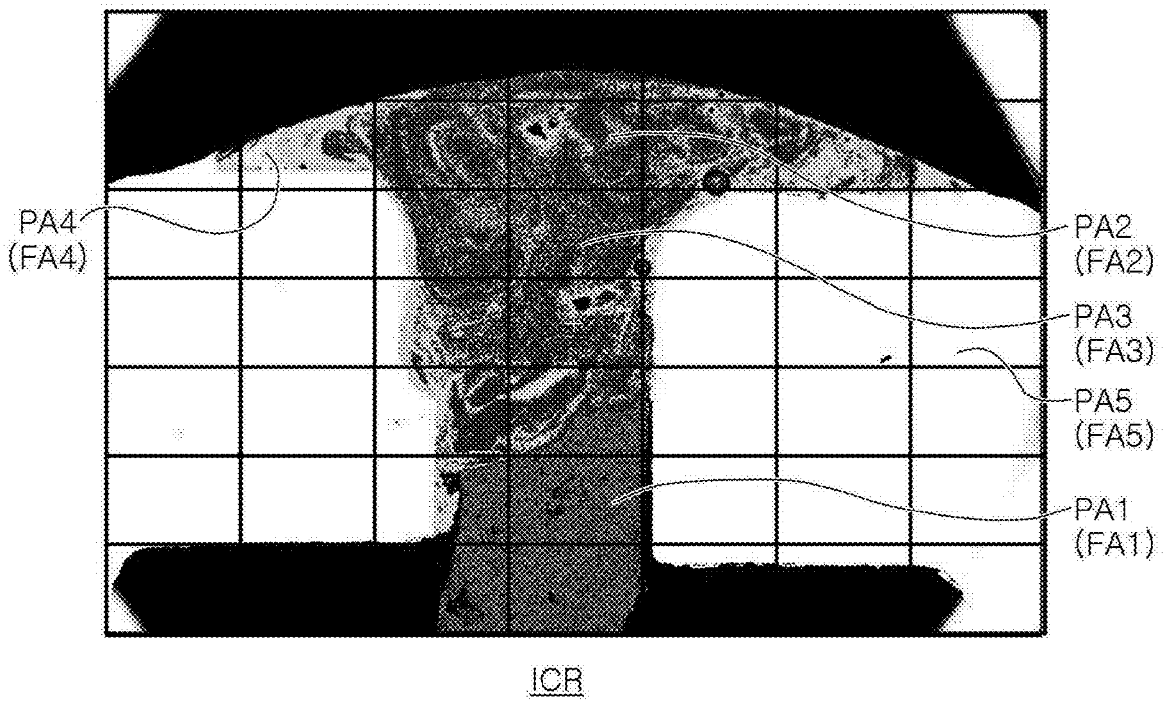
FIG. 11 is an example diagram of a colorization image.

FIG. 11 is an example diagram for a color image.

Referring to FIG. 6 and FIG. 11, with respect to the colors of respective feature areas FA to FA5 for the colorization image (ICR) generated by the first image processing unit 710, gray may be matched to the first feature area FA1 corresponding to the PA1 area of FIG. 6 in the colorization image (ICR), blue may be matched to the second feature area FA2 corresponding to the PA2 area of FIG. 6 in the colorization image (ICR), green may be matched to the third feature area FA3 corresponding to the PA3 area of FIG. 6 in the colorization image (ICR), yellow may be matched to the fourth feature area FA4 corresponding to the PA4 area of FIG. 6 in the colorization image (ICR), and white may be matched to the fifth feature area FA5 corresponding to the PA5 area of FIG. 6 in the colorization image (ICR).

In this disclosure, the description of the colors for respective feature areas FA to FA5 is an example, and thus, the present disclosure is not necessary to be limited to the above example.

Figure 12:
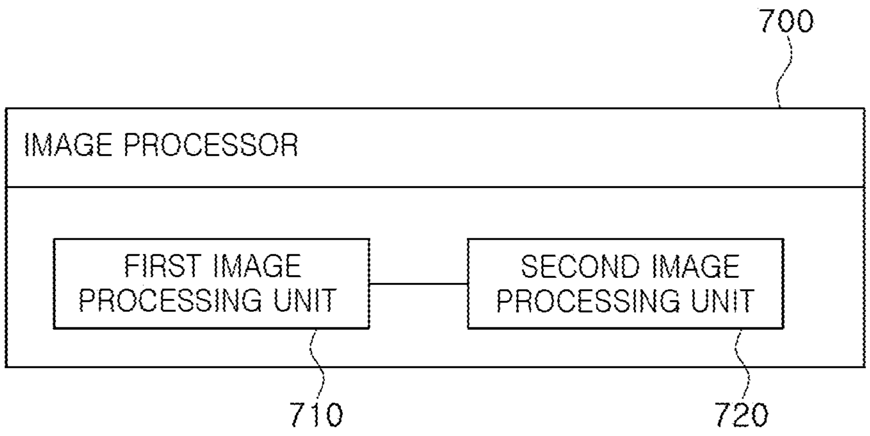
FIG. 12 is an example diagram of an image processor.

FIG. 12 is an example diagram of an image processor.

Referring to FIG. 12, the image processor 700 may include a second image processing unit 720.

The second image processing unit 720 may extract a plurality of color images distinguished by the plurality of respective first to fifth feature areas FA1 to FA5 for the intermetallic compound (OBT) using the colorization image (ICR).

For example, the extracted plurality of color images may include a first color image including a color corresponding to a first feature area FA1, a second color image including a color corresponding to a second feature area FA2, a third color image including a color corresponding to a third feature area FA3, a fourth color image including a color corresponding to a fourth feature area FA4, and a fifth color image including a color corresponding to a fifth feature area FA5. This will be described with reference to FIG. 14.

Figure 13:
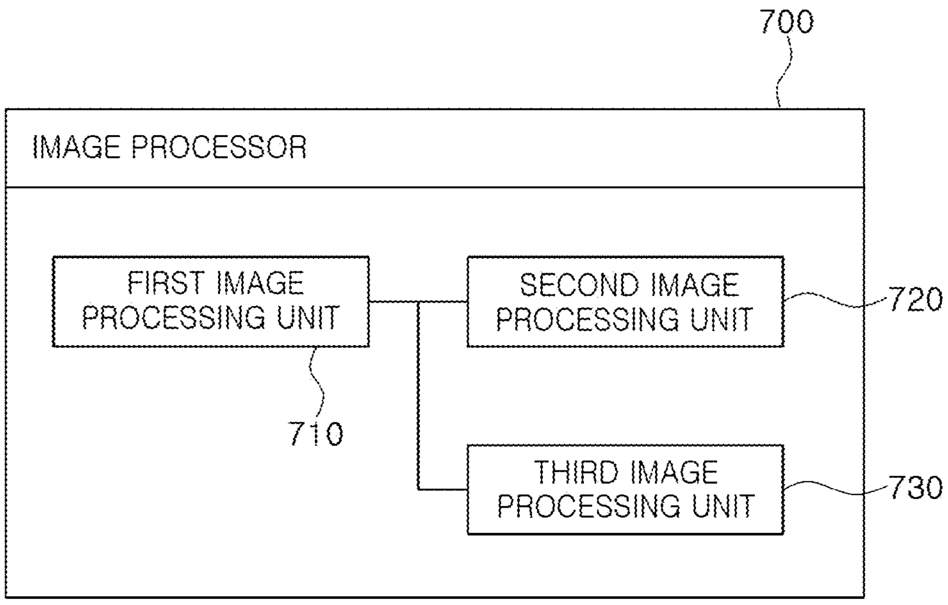
FIG. 13 is an example diagram of an image processor.

FIG. 13 is an example diagram of an image processor.

Referring to FIG. 13, the image processor 700 may include a third image processing unit 730.

The third image processing unit 730 may calculate an area occupied by each of the plurality of feature areas FA1 to FA5 using the colorization image (ICR).

For example, the third image processing unit 730 counts pixels corresponding to respective colors for the plurality of respective color images, and counts pixels included in each of the plurality of feature areas FA1 to FA5 with respect to all pixels, thereby calculating the relative occupied area ratios for the plurality of respective feature areas FA1 to FA5. This will be described with reference to FIG. 15.

Figure 14:
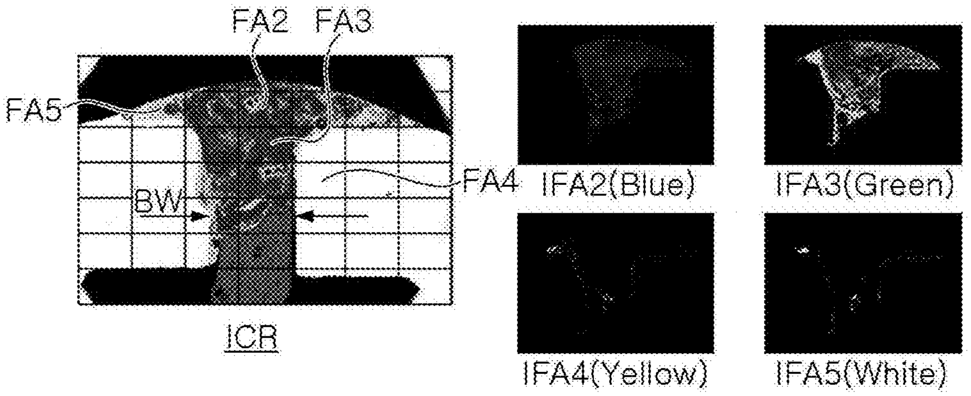
FIG. 14 is an example diagram of a colorization image (ICR) and a plurality of color images.

FIG. 14 is an example of a colorization image (ICR) and a plurality of color images.

Referring to FIG. 11, FIG. 12, and FIG. 14, a plurality of color images may be extracted from a colorization image (ICR), and the plurality of color images may include a first color image including a color (for example, gray) corresponding to a first feature area FA1, a second color image including a color (for example, blue) corresponding to a second feature area FA2, a third color image including a color (for example, green) corresponding to a third feature area FA3, a fourth color image including a color (for example, yellow) corresponding to a fourth feature area FA4, and a fifth color image including a color (for example, white) corresponding to a fifth feature area FA5.

FIG. 14 illustrates examples of a second color image IFA2 (for example, blue), a third color image IFA3 (for example, green), a fourth color image IFA4 (for example, yellow) and a fifth color image IFA5 (for example, white) extracted from the colorization image (ICR).

Figure 15:
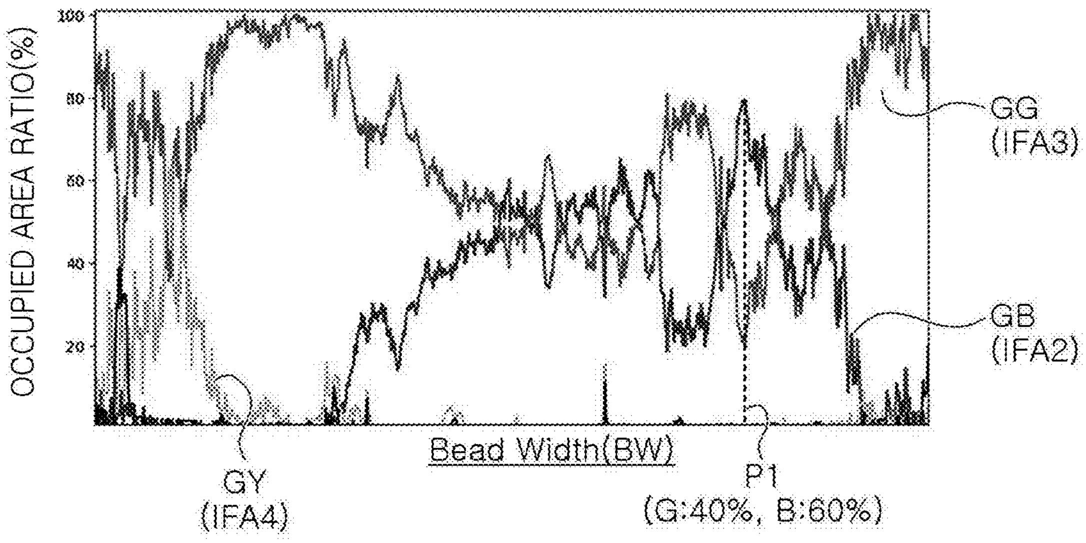
FIG. 15 is a distribution graph of an occupancy area ratio of respective colors with respect to bead widths of intermetallic compounds (IMCs).

FIG. 15 is a distribution graph of the occupied area ratio of respective colors with respect to the bead width of the intermetallic compound (IMC).

The distribution graph illustrated in FIG. 15 is a graph of the occupied area ratio by position of the bead width corresponding to each of the second color image IFA2 (for example, blue), the third color image IFA3 (for example, green), and the fourth color image IFA4 (for example, yellow) with respect to the bead width (BW) of FIG. 14.

In FIG. 15, the GB graph is a blue color occupied ratio graph corresponding to the second color image IFA2 (for example, blue), the GG graph is a green color occupied ratio graph corresponding to the third color image IFA3 (for example, green), and the GY graph is a yellow color occupied ratio graph corresponding to the fourth color image IFA4 (for example, yellow).

For example, it can be seen that for the occupied area ratio in P1 of the graph of FIG. 15, the ratio of green (G) and blue (B) is 40% to 60%.

As described above, according to an embodiment of the present disclosure, the occupied area ratio for each color for the weld may be confirmed, and accordingly, the thermochemical characteristics for each area of the weld may be known, and further, the soundness of the weld related to crack susceptibility or crack resistance, and the like, may be confirmed.

Hereinafter, with reference to FIGS. 16 to 21, a method of analyzing compositions of intermetallic compounds will be described. In the present disclosure, the description of the method of analyzing a composition of an intermetallic compound and the description of the apparatus for analyzing a composition of an intermetallic compound may be applied complementarily or in common, unless they are mutually exclusive. Accordingly, overlapping descriptions may be omitted. Hereinafter, the main process of a method of analyzing a composition of an intermetallic compound will be described.

Figure 16:
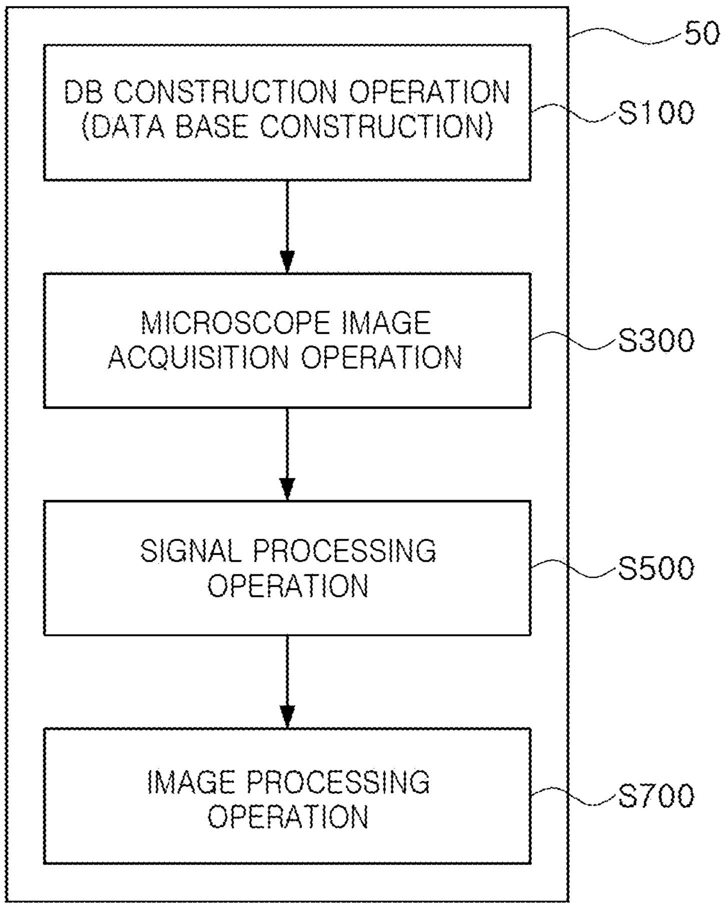
FIG. 16 is an example diagram of an operation of a method of analyzing a composition of an intermetallic compound according to an embodiment.

FIG. 16 is an illustrative operation diagram of a method of analyzing a composition of an intermetallic compound according to an embodiment.

Referring to FIG. 16, a method of analyzing a composition of an intermetallic compound according to an embodiment may include a DB construction operation (S100), a microscope image acquisition operation (S300), a signal processing operation (S500), and an image processing operation (S700).

In the DB construction operation (S100), a apparatus 50 for analyzing a composition of an intermetallic compound may construct a database 100 that stores data (PI) of a plurality of feature areas FA1 to FA5 matched to respective composition ratios (CR) for intermetallic compounds (IMCs) generated during dissimilar metal welding, data (BI) of a plurality of brightness ranges (BR), color data (HI), and phase data (PHI) corresponding to each of the plurality of feature areas FA1 to FA5.

In the microscope image acquisition operation (S300), the apparatus 50 for analyzing a composition of an intermetallic compound may acquire an electron microscope image (IEM) including a brightness value for an intermetallic compound (OBT) that is an analysis target.

In the signal processing operation (S500), the apparatus 50 for analyzing a composition of an intermetallic compound may extract a unit brightness value BV1 corresponding to each preset image basic unit (RU) from the electron microscope image (IEM), and search for a feature area, a brightness range, and color data (HI) matched to the unit brightness value BV1 from the database 100.

In the image processing operation (S700), the apparatus 50 for analyzing a composition of an intermetallic compound may apply the searched color data (HI) to the electron microscope image (IEM) to generate a colorization image (ICR).

The database 100 may further include phase data (PHI) and microstructural feature data (MSF) according to each composition ratio (CR), in addition to the data (PI) of the plurality of feature areas FA1 to FA5 matched to respective composition ratios (CR) for intermetallic compounds (IMCs), the data (BI) of the plurality of brightness ranges (BR) corresponding to the plurality of respective feature areas FA1 to FA5, the color data (HI), and the phase data (PHI).

Figure 17:
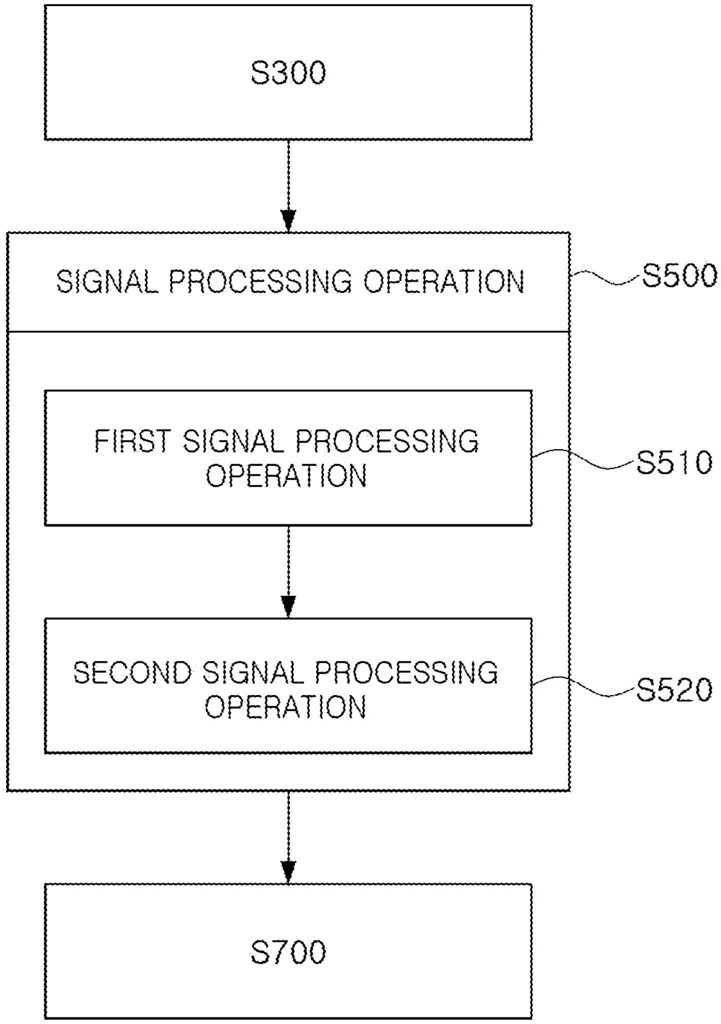
FIG. 17 is an example diagram of operations of a signal processing stage.

FIG. 17 is an example diagram of operations of a signal processing operation.

Referring to FIG. 17, a signal processing operation (S500) may include a first signal processing operation (S510) and a second signal processing operation (S520).

In the first signal processing operation (S510), a apparatus 50 for analyzing a composition of an intermetallic compound may extract a unit brightness value BV1 corresponding to each preset image basic unit (RU) from the electron microscope image (IEM), and correct the unit brightness value BV1 to generate a correction brightness value BV2.

In the second signal processing operation (S520), the apparatus 50 for analyzing a composition of an intermetallic compound may check the brightness range data (BI) matched to the correction brightness value BV2 from the database 100 and search for the corresponding color data (HI).

Figure 18:
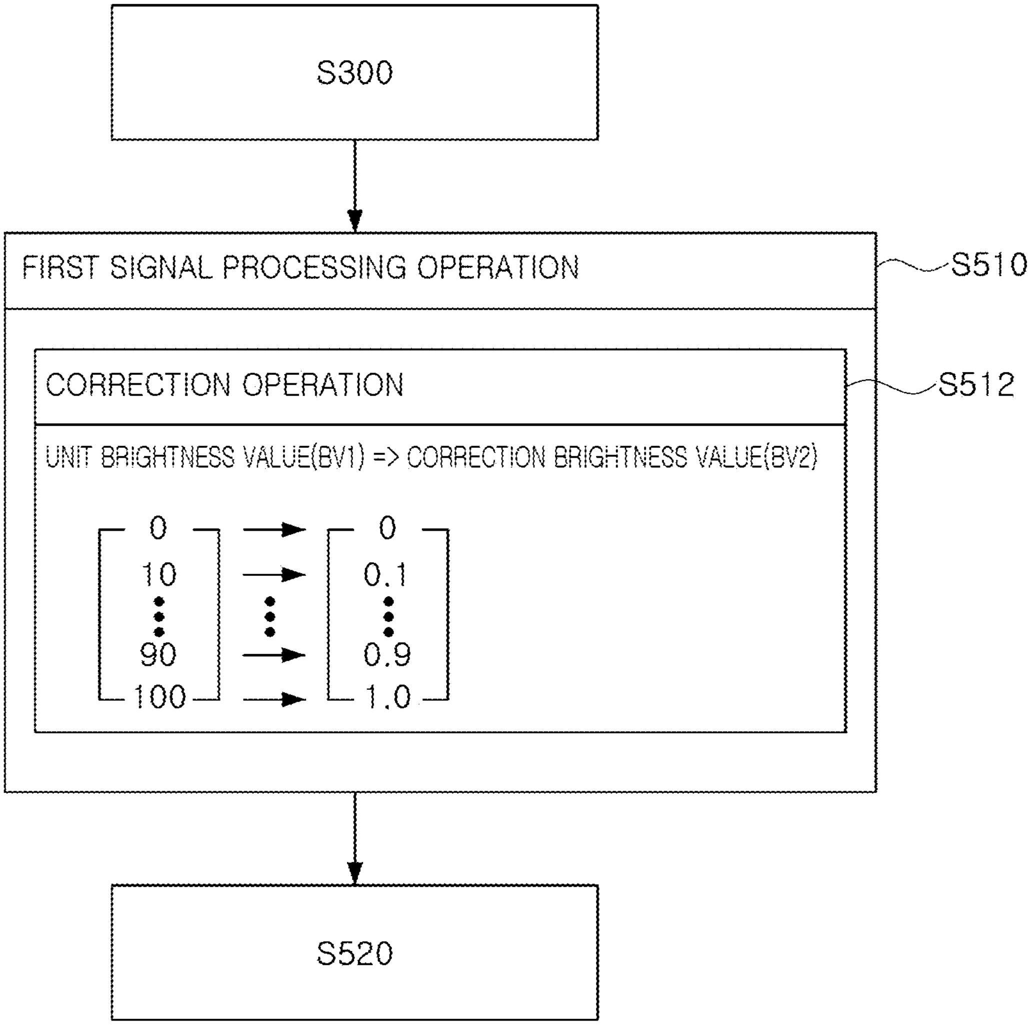
FIG. 18 is an example diagram of operations of a first signal processing stage.

FIG. 18 is an example diagram of operations of the first signal processing operation.

Referring to FIG. 18, the first signal processing operation (S510) may include a correction operation (S512).

In the correction operation (S512), the apparatus 50 for analyzing a composition of an intermetallic compound may correct the unit brightness value BV1 of the intermetallic compound (OBT) to a corresponding correction brightness value BV2 corresponding to a composition ratio of copper (Cu) and aluminum (Al) within the range of a preset correction brightness value BV2 when the intermetallic compound (OBT) is a compound of copper (Cu) and aluminum (Al).

Figure 19:
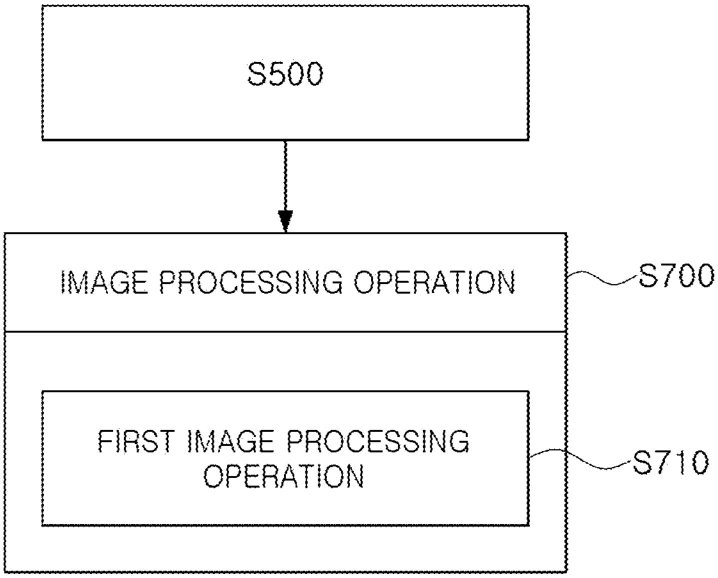
FIG. 19 is an example diagram of operations of an image processing stage.

FIG. 19 is an example diagram of operations of the image processing operation.

Referring to FIG. 19, the image processing operation (S700) may include a first image processing operation (S710).

In the first image processing operation (S710), the apparatus 50 for analyzing a composition of an intermetallic compound may apply the searched color data (HI) to the electron microscope image (IEM) to generate a colorization image (ICR).

Figure 20:
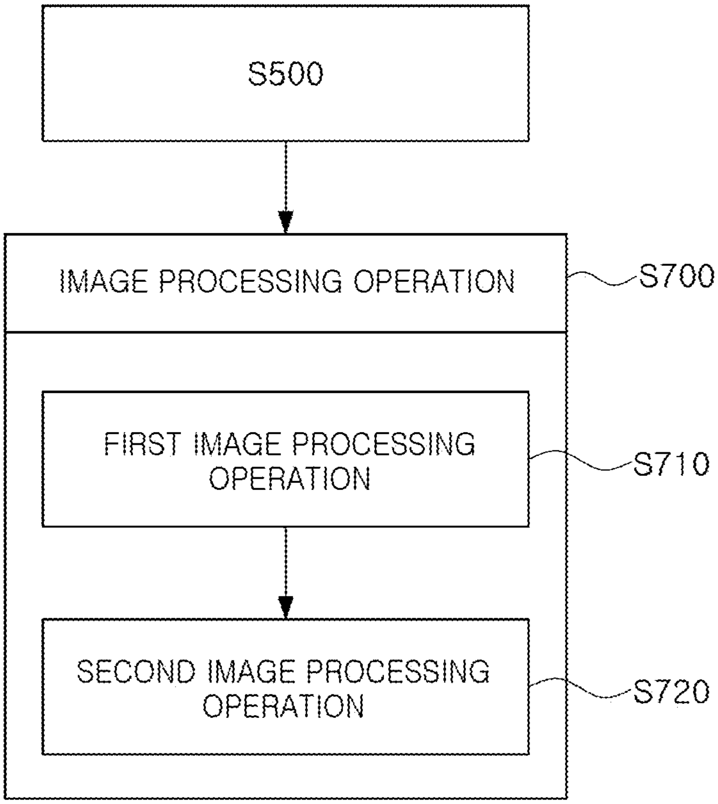
FIG. 20 is an example diagram of operations of an image processing stage.

FIG. 20 is an example of operations of an image processing operation.

Referring to FIG. 20, the image processing operation (S700) may further include a second image processing operation (S720).

In the second image processing operation (S720), the apparatus 50 for analyzing a composition of an intermetallic compound may extract a plurality of color images distinguished by the plurality of feature areas FA1 to FA5 with respect to the intermetallic compound (OBT), using the colorization image (ICR).

Figure 21:
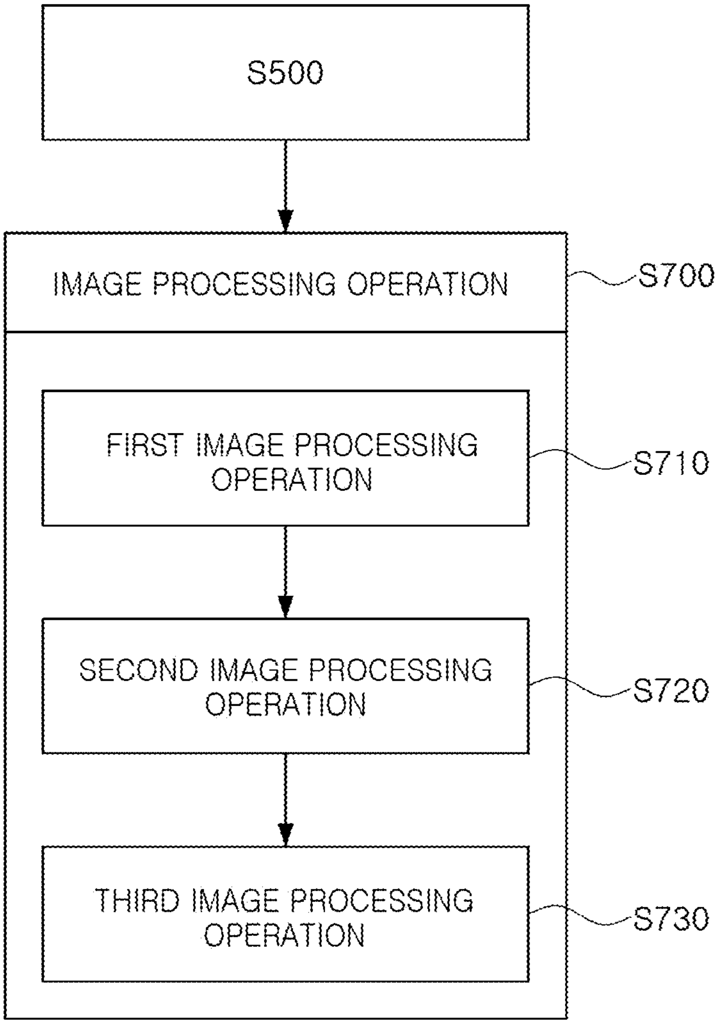
FIG. 21 is an example diagram of operations of an image processing stage.

FIG. 21 is an example of operations of the image processing operation.

Referring to FIG. 21, the image processing operation (S700) may further include a third image processing operation (S730).

In the third image processing operation (S730), the apparatus 50 for analyzing a composition of an intermetallic compound may calculate areas occupied by the plurality of respective feature areas FA1 to FA5 using the colorization image (ICR).

The above description is merely an example of applying the principles of the present disclosure, and other configurations may be further included without departing from the scope of the present disclosure.

As set forth above, according to an example embodiment, by utilizing a database (DB) storing in advance relevant data necessary for analysis of intermetallic compounds (IMCs), quantitative analysis such as colorization by feature area for intermetallic compounds (OBT) as an analysis target may be performed, thereby providing an effect of performing analysis of intermetallic compounds (IMCs) of a weld joint more accurately and quickly.

Only specific examples of implementations of certain embodiments are described. Variations, improvements and enhancements of the disclosed embodiments and other embodiments may be made based on the disclosure of this patent document.

What is claimed is:

1. A apparatus for analyzing a composition of an intermetallic compound, comprising:

a database storing data of a plurality of feature areas matched to respective composition ratios, a plurality of brightness range data corresponding to the plurality of respective feature areas, and color data, for an intermetallic compound generated during welding of dissimilar metals;

a microscope image acquisition unit acquiring an electron microscope image including a brightness value for the intermetallic compound to be analyzed;

a signal processor extracting a unit brightness value corresponding to each preset image basic unit from the electron microscope image and searching for color data of a corresponding feature area from the database based on the unit brightness value; and an image processor applying searched color data to the electron microscope image and generating a colorization image.

2. The apparatus of claim 1, wherein the database further includes phase data and microstructural feature data according to the respective composition ratios for the intermetallic compound generated during the welding of dissimilar metals.

3. The apparatus of claim 1, wherein the microscope image acquisition unit acquires the electron microscope image of the intermetallic compound through an SEM or a TEM.

4. The apparatus of claim 1, wherein the signal processor includes:

a first signal processing unit extracting the unit brightness value corresponding to each preset image basic unit from the electron microscope image, and generating a correction brightness value by correcting the unit brightness value; and a second signal processing unit checking brightness range data matched to the correction brightness value from the database and searching for corresponding color data.

5. The apparatus of claim 4, wherein the first signal processing unit includes a brightness correction unit correcting the unit brightness value of the intermetallic compound to a corresponding correction brightness value corresponding to a composition ratio of copper and aluminum within a preset correction brightness value range when the intermetallic compound is a compound of the copper and the aluminum.

6. The apparatus of claim 1, wherein the image processor includes a first image processing unit applies the searched color data to the electron microscope image and generates the colorization image.

7. The apparatus of claim 6, wherein the image processor further includes a second image processing unit extracting a plurality of color images distinguished by the plurality of feature areas for the intermetallic compound, using the colorization image.

8. The apparatus of claim 6, wherein the image processor further includes a third image processing unit calculating an area occupied by each of the plurality of feature areas using the colorization image.

9. A method of analyzing a composition of an intermetallic compound, comprising:

a DB construction operation of constructing, by a apparatus for analyzing a composition of an intermetallic compound, a database storing data of a plurality of feature areas matched to respective composition ratios, and color data and a plurality of brightness range data corresponding to the plurality of respective feature areas, for the intermetallic compound generated during welding of dissimilar metals;

a microscope image acquisition operation of acquiring an electron microscope image including a brightness value for the intermetallic compound as an analysis target, by the apparatus for analyzing a composition of an intermetallic compound;

a signal processing operation of extracting a unit brightness value corresponding to each of preset image basic units from the electron microscope image and searching for color data of a corresponding feature area from the database based on the unit brightness value, by the apparatus for analyzing a composition of an intermetallic compound; and an image processing operation of applying searched color data to the electron microscope image and generating a colorization image by the apparatus for analyzing a composition of an intermetallic compound.

10. The method of claim 9, wherein the database further includes phase data and microstructural feature data according to the respective composition ratios for the intermetallic compound generated during the welding of dissimilar metals.

11. The method of claim 9, wherein the signal processing operation includes, a first signal processing operation of extracting a unit brightness value corresponding to each preset image basic unit from the electron microscope image and generating a correction brightness value by correcting the unit brightness value; and a second signal processing operation of checking brightness range data matched to the correction brightness value and searching for corresponding color data, from the database.

12. The method of claim 11, wherein the first signal processing operation includes, when the intermetallic compound is a compound of copper and aluminum, a correction operation of correcting the unit brightness value for the intermetallic compound to a corresponding correction brightness value corresponding to a composition ratio of the copper and the aluminum within a preset correction brightness value range.

13. The method of claim 9, wherein the image processing operation includes a first image processing operation of applying searched color data to the electron microscope image and generating a colorization image.

14. The method of claim 13, wherein the image processing operation further includes a second image processing operation of extracting a plurality of color images distinguished by the plurality of feature areas for the intermetallic compound, using the colorization image.

15. The method of claim 13, wherein the image processing operation further includes a third image processing operation of calculating an area respectively occupied by the plurality of feature areas using the colorization image.

* * * * *